United States Patent [19]

Moore

[11] 4,016,275

[45] Apr. 5, 1977

[54] INSECTICIDAL HYDROCARBYL SULFENYLMERCAPTO PYRIMIDINES

[75] Inventor: Joseph E. Moore, Richmond, Calif.

[73] Assignee: Chevron Research Company, San Francisco, Calif.

[22] Filed: July 3, 1975

[21] Appl. No.: 592,831

Related U.S. Application Data

[60] Continuation-in-part of Ser. No. 461,578, April 17, 1974, Pat. No. 3,896,225, which is a division of Ser. No. 201,185, Nov. 22, 1971, Pat. No. 3,821,222.

[52] U.S. Cl. .......................... 424/251; 260/251 R
[51] Int. Cl.² .................. A01N 9/00; C07D 239/22
[58] Field of Search ................ 260/251 R; 424/251

[56] References Cited

UNITED STATES PATENTS

| | | | |
|---|---|---|---|
| 2,356,710 | 8/1944 | Stiteler | 260/251 R |
| 2,839,446 | 6/1958 | Margot et al. | 424/251 |
| 3,896,225 | 7/1975 | Moore | 424/251 |

*Primary Examiner*—Lewis Gotts
*Assistant Examiner*—D. R. Phillips
*Attorney, Agent, or Firm*—J. A. Buchanan, Jr.; Dix A. Newell; Raymond Owyang

[57] ABSTRACT

Compounds of the formula

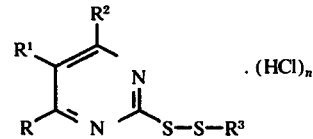

wherein R, $R^1$ and $R^2$ are hydrogen, halogen, hydroxy, alkyl or alkenyl optionally substituted with halogen atoms and $R^3$ is a haloalkyl, haloalkenyl or aryl group, possess morphogenetic hormonal mimetic insecticidal activity.

4 Claims, No Drawings

INSECTICIDAL HYDROCARBYL SULFENYLMERCAPTO PYRIMIDINES

RELATED APPLICATIONS

This application is a continuation-in-part of application Ser. No. 461,578, filed Apr. 17, 1974, now U.S. Pat. No. 3,896,225, which in turn is a division of application Ser. No. 201,185, filed Nov. 22, 1971, now U.S. Pat. 3,821,222.

BACKGROUND OF THE INVENTION

Field of the Invention

The present invention is concerned with insecticidal compounds which have morphogenetic hormonal mimetic activity. Compounds having morphogenetic hormonal mimetic activity exert a disrupting influence upon the normal development of insects. These compounds interfere with the normal metamorphosis of the pest insects and result in the formation of individual insects of the treated species which develop abnormally and are non-viable or sterile. This ultimately leads, indirectly at least, to the destruction of the insect population.

Prior Art

U.S. Pat. No. 2,839,446 discloses certain pyrimidine derivatives, particularly trichloromethylsulfenylmercapto pyrimidines, and their use in the control of fungi.

DESCRIPTION OF THE INVENTION

The novel compounds of the present invention can be represented by the general formula

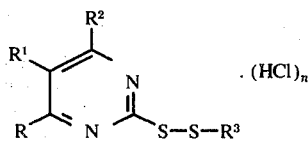

wherein R, $R^1$ and $R^2$ are individually hydrogen, halogen of atomic number 9 to 35 (fluorine, chlorine or bromine), hydroxy, alkyl of 1 to 6 carbon atoms substituted with 0 to 4 halogen atoms of atomic number 9 to 35 or alkenyl of 2 to 6 carbon atoms substituted with 0 to 4 halogen atoms of atomic number 9 to 35; $R^3$ is a haloalkyl or haloalkenyl group of 2 to 10 carbon atoms substituted with 1 to 5 halogen atoms of atomic number 9 to 35; or phenyl substituted with 0 to 2 halogen atoms of atomic number 9 to 35 or alkyl groups of 1 to 4 carbon atoms.

Preferably $R^1$ is hydrogen, R and $R^2$ are individually hydrogen, hydroxy or alkyl of 1 to 4 carbon atoms and $R^3$ is haloalkyl or haloalkenyl of 2 to 4 carbon atoms substituted with 1 to 5 halogen atoms of atomic number 9 to 35, particularly chlorine, or phenyl substituted with 0 to 2 halogen atoms of atomic number 9 to 35, particularly chlorine. More preferably R is hydrogen or methyl, $R^1$ is hydrogen, $R^2$ is hydrogen, hydroxy or alkyl of 1 to 3 carbon atoms and $R^3$ is haloalkyl of 2 to 4 carbon atoms substituted with 2 to 5 chlorine atoms or phenyl substituted with 1 to 2 chlorine atoms. The most preferred $R^3$ groups are tetrachloroethyl, 1,1-dimethyl-2,2-dichloroethyl or p-chlorophenyl.

The compounds described above possess juvenile hormonal mimetic activity. In particular, the compounds wherein $R^3$ is haloalkyl or haloalkenyl group of up to 10 carbon atoms substituted with 1 to 5 halogen atoms of atomic number 9 to 35 possess juvenile hormonal mimetic activity. Thus, compounds where $R^3$ is methyl substituted with halogen atoms also have juvenile hormonal mimetic activity.

Representative groups which R, $R^1$ and $R^2$ may represent are hydrogen, fluorine, chlorine, bromine, hydroxyl, methyl, ethyl, n-propyl, isopropyl, n-butyl, sec-butyl, t-butyl, pentyl, hexyl, allyl, crotyl, 2-propenyl, chloromethyl, trichloromethyl, bromomethyl, 2-fluoroethyl, etc.

Preferably the representative groups for R, $F^1$ and $R^2$ will be hydrogen, hydroxy, methyl, ethyl, propyl and butyl.

Representative groups with $R^3$ may represent include 1-chloroethyl, 1,1-dichloroethyl, 1,1,2-trichloroethyl, 2,2,2-trichloroethyl, 1,1,2,2-tetrachloroethyl, 1,2,2,2-tetrachloroethyl, pentachloroethyl, trichlorovinyl, 1,1-dimethyl-2,2,2-trichloroethyl, 1,1-dimethyl-2,2-dichloroethyl, 1,1,2,2,-tetrachloropropyl, 1,2,3-trichloropropyl, 1,1-difluoroethyl, 1,1,2-tribromoethyl, 1-bromo-2-chloroethyl, 1,1-dichlorohexyl, phenyl, naphthyl, 4-chlorophenyl, 2-chlorophenyl, 2,4-dichlorophenyl, 3,4-dichlorophenyl, 2-bromophenyl, 3-fluorophenyl, 2-methyl-4-chlorophenyl, 4-butylphenyl, etc.

When the compounds are used as insecticides, $R^3$ may also represent chloromethyl, dichloromethyl, trichloromethyl, bromochloromethyl, trifluoromethyl, dibromomethyl, etc.

Typical compounds of the present invention include the following:

2-(1,1,2,2-tetrachloroethylsulfenylmercapto)-4-methyl pyrimidine,
2-(1,1,2,2-tetrachloroethylsulfenylmercapto)-4-chloromethyl-6-hydroxy pyrimidine,
2-(1,1,2,2-tetrachloroethylsulfenylmercapto)-4,6-dimethyl pyrimidine,
2-(1,1,2,2-tetrachloroethylsulfenylmercapto)-4-chloro pyrimidine,
2-(1,1,2,2-tetrachloroethylsulfenylmercapto)-4,5,6-trimethyl pyrimidine,
2-(1,1,2,2-tetrachloroethylsulfenylmercapto)-4-hydroxy pyrimidine,
2-(1,1,2,2-tetrachloroethylsulfenylmercapto)-4-hydroxy-6-methyl pyrimidine,
2-(1,1,2,2-tetrachloroethylsulfenylmercapto)-4-ethyl-6-methyl pyrimidine,
2-(1,1,2,2-tetrachloroethylsulfenylmercapto)-4-allyl pyrimidine,
2-(1,1,2,2-tetrachloroethylsulfenylmercapto)-4-hydroxy-6-ethyl pyrimidine,
2-(1,1,2,2-tetrachloroethylsulfenylmercapto)-4-hydroxy-6-n-butyl pyrimidine,
2-(1,1,2,2-tetrachloroethylsulfenylmercapto)-4-methyl-6-crotyl pyrimidine,
2-(1,1,2,2-tetrachloroethylsulfenylmercapto)-4-propyl pyrimidine,
2-(1,1,2-trichloroethylsulfenylmercapto)-4-methyl pyrimidine,
2-(1,2,2,2-tetrachloroethylsulfenylmercapto)-4-methyl-6-hydroxy pyrimidine,
2-pentachloroethylsulfenylmercapto-4-methyl pyrimidine,
2-(1,1-dibromo-2,2-dichloroethylsulfenylmercapto)-4-hydroxy-6-methyl pyrimidine, 2-trichlorovinylsulfenylmercapto-4,6-dimethyl pyrimidine,
2-(1,2-dichlorovinylsulfenylmercapto)-4,6-diethyl pyrimidine,
2-(1,1,2,2-tetrachloropropylsulfenylmercapto)-4-hydroxy pyrimidine,
2-(1,2,3-trichloropropylsulfenylmercapto) pyrimidine,
2-(1,2,3-trichloropropylsulfenylmercapto)-6-ethyl pyrimidine,
2-pentachloroethylsulfenylmercapto-4-methyl-6-isopropyl pyrimidine,
2-(1,1-dimethyl-2,2-dichloroethylsulfenylmercapto)-4-propyl pyrimidine,
2-(1,1-dimethyl-2,2,-dichloroethylsulfenylmercapto)-4-hydroxy-6-methyl pyrimidine,
2-(1,1-dimethyl-2,2-dibromoethylsulfenylmercapto)-4-butyl pyrimidine,
2-(1,1,2,2-tetrachloroethylsulfenylmercapto) pyrimidine,
2-(phenylsulfenylmercapto)-4,5-dimethyl pyrimidine,
2-(4-chlorophenylsulfenylmercapto)-4-methyl-6-hydroxy pyrimidine,
2-(4-chlorophenylsulfenylmercapto)-6-hydroxy pyrimidine,
2-(4-chlorophenylsulfenylmercapto)-4,5,6-trimethyl pyrimidine,
2-(4-chlorophenylsulfenylmercapto)-4-allyl pyrimidine,
2-(3,4-dichlorophenylsulfenylmercapto)-4-methyl-6-hydroxy pyrimidine,
2-(3-methylphenylsulfenylmercapto)-4-hydroxy-6-methyl pyrimidine,
2-(2-fluoro-4-chlorophenylsulfenylmercapto)-4-methyl pyrimidine,
2-(2-methyl-4-chlorophenylsulfenylmercapto)-4-hydroxy pyrimidine,
2-trichloromethylsulfenylmercapto)-4-hydroxy-6-methyl pyrimidine, etc.

The hydrochlorides of the above-named compounds are also included.

The compounds of this invention are prepared by the reaction of a sulfenyl chloride and an appropriate 2-mercapto pyrimidine or 2-mercapto pyrimidine hydrochloride. The reaction may be written as follows:

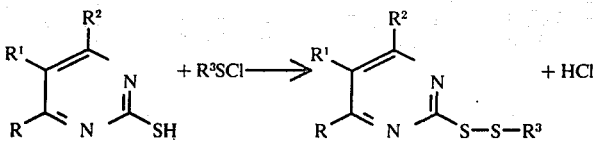

wherein R, R¹, R² and R³ are as previously defined. When the 2-mercapto pyrimidine starting material is the hydrochloride salt, two mols of hydrogen chloride are released during the reaction.

The reaction is usually carried out in a solvent. The reaction involving 2-mercapto pyrimidine may be carried out in dichloromethane, chloroform, benzene, xylene, ethyl acetate or a liquid alkanoic acid. The reaction involving a 2-mercapto pyrimidine hydrochloride is preferably carried out in acetic acid as the solvent. The quantity of solvent is not critical, and generally varies in weight from 5 to 50 times the weight of the pyrimidine compound. Usually the pyrimidine compound is dissolved or slurried in the solvent, and then unsolvated sulfenyl chloride in an amount at least equal in mols to the pyridine is added rapidly. The reaction temperature may vary from 20° to 100° C. In order to completely remove the by-product hydrogen chloride, a temperature of 70° to 100° C is preferred. When a hydrochloride product is desired, the reaction temperature is kept lower, e.g. below 80° C. The time of reaction is dependent upon the temperature and the nature of the reactants; however, reaction is continued until all of the insoluble starting material has disappeared. Usually the reaction is complete in from 0.1 to 10 hours, more often 0.5 to 1 hour.

The product is recovered from the reaction mixture by filtering hot and then evaporating off the solvent. The resulting crude product may be used as is, or it may be purified by crystallization or by chromatography. Crystallization is readily accomplished by cooling a solution of the crude product. Solvents for crystallization are preferably mixtures of aromatic hydrocarbons such as benzene, toluene, etc., with an aliphatic hydrocarbon such as pentane, hexane, etc. The ratio of the two may vary from 1:2 to 2:1 by volume.

The compounds of this invention may also be prepared by the process of U.S. Pat. No. 2,839,446, which is concerned with the 2-trichloromethylsulfenylmercapto pyrimidines.

EXAMPLES

The subject invention can be more fully understood by reference to the following examples. Unless otherwise indicated, percentages are by weight.

EXAMPLE 1

Preparation of 2-(1,1,2,2-tetrachloroethylsulfenylmercapto)-4-methyl pyridine

A suspension was prepared by mixing 3.4 g (0.02 mol) 2-mercapto-4-methyl pyrimidine hydrochloride in 100 ml of acetic acid. Then 5.0 g (0.02 mol) of tetrachloroethylsulfenylchloride was added to this suspension all at once. The resulting mixture was stirred at the reflux temperature for 3 minutes. At the end of this time the reaction mixture was filtered while hot. The filtrate was evaporated to 10 ml by volume. This material was then diluted with 100 ml of benzene and 75 ml of hexane and cooled to 0° C. The precipitate was removed by filtration and discarded. The filtrate was evaporated to give a liquid which crystallized upon standing. The crystals were separated by filtration and after drying weighed 3.3 g. The product, 2-(1,1,2,2-tetrachloroethylsulfenylmercapto)-4-methyl pyrimidine, had a melting point of 54°–56° C. Analysis was as follows: %Cl, calc. 43.8, found 43.2; %S, calc. 19.8, found 18.0.

The infrared spectrum had strong adsorption bands at 6.35, 6.8, 7.5, 8.3, 12.0, 12.45, 13.2 and 14.05 microns.

EXAMPLE 2

Preparation of
2-(1,1,2,2-tetrachloroethylsulfenylmercapto)-4-hydroxy-6-propyl pyrimidine hydrochloride To a slurry of 5.0 g (0.029 mol) of 2-mercapto-4-hydroxy-6-propyl pyrimidine in 50 ml of 1,2-dimethoxyethane was added 6.9 g (0.029 mol) of 1,1,2,2-tetrachloroethylsulfenyl chloride. The resulting mixture was heated at the reflux temperature for 10 minutes, and then filtered while still hot. The solvent was removed by evaporation under reduced pressure to give 8.8 g of 1,1,2,2-tetrachloroethylsulfenylmercapto)-4-hydroxy-6-propyl pyrimidine hydrochloride having a melting point of 142°-144° C. Analysis was as follows: %Cl, calc., 43.8, found 43.0; %S, calc. 15.8, found 15.5.

Infrared analysis showed strong adsorption bands at 6.15, 6.35, 6.75, 7.2, 7.65, 11.7, 12.4 and 13.3 microns.

Other compounds of the present invention were made by similar reactions. These are listed in Table I.

UTILITY

The compounds of the invention are useful as morphogenetic hormonal mimetic insecticides, particularly against insects such as cabbage looper larvae, alfalfa weevil larvae, yellow mealworm, kissing bug and mosquitos.

The compounds are very potent and are used at extremely low concentrations. For example, compositions containing 100 ppm to 0.01 ppm are effective for inhibiting or interfering with the normal metamorphosis of insects. However, the effective concentration depends in part on the mode of application and the particular insect.

The compounds may be applied in either liquid or solid formulations to the pre-adult insects or their habitats. For example, they may be sprayed or otherwise applied directly to plants or aqueous bodies so as to effect control of insects coming into contact therewith.

Formulations of the compounds of this invention will comprise a metamorphosis-inhibiting amount of one or more of the compounds and a biologically inert carrier. Usually they will also contain a wetting agent. Solid carriers such as clay, talc, sawdust, alfalfa meal, and the like may be used in such formulations. Liquid diluents which may be used with these compounds include water, aliphatic and aromatic solvents. In addition, these formulations may contain other compatible pesticides, fillers, stabilizers, attractants and the like.

The concentration of the active ingredient to be used with inert carriers, either solid or liquid carriers, will be dependent upon many factors, such as the particular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001% by weight to as high as 50% by weight or higher. Economically, of course, it is desirable to use lower concentrations of this active ingredient.

The terms "insecticide" and "insect" as used herein refer to their broad and commonly understood usage rather than to those creatures which in the strict biological sense are classified as insects. Thus, the term "insect" is used not only to include small invertebrate animals belonging to the class Insecta, but also to other related classes of arthropods whose members are segmented invertebrates having more or fewer than six legs, such as spiders, mites, ticks, centipedes, worms, and the like.

EXAMPLE 3

To show the insecticidal activity of the subject compounds, particularly the juvenile hormonal mimetic activity, several different pests in a pre-adult stage of development were contacted with a solution of the test compound. The treated insects were then observed as to the compounds'effect upon the development of the succeeding stages (juvenilization), including egg laying and egg hatching to give a new generation. Mortality readings were taken.

Tests were carried out on the following pests: dock beetle (*Gastrophysa cyanes*, cabbage looper (*Trichoplusia ni*) yellow fever mosquito (*Aedes aegypti*).

For the dock beetle test, an acetone solution containing 20 micrograms in 1 microliter of solution was topically applied to the abdomen of a late fifth-stage (last-stage) larva. Usually 10 to 20, preferably 20, larvae were treated. Following treatment, the larvae were kept in an incubator until the adult emerged (or attempted to emerge). At this time, a count was made of the dead pupae. The live specimens were examined under a microscope for juvenilization. The number of juvenile adults per total number tested were recorded, and is given in Table II as percent juvenilization. Also, the degree of juvenilization was measured, based on the following:

0 = normal-appearing adult
1 = crumpled elytra in the adult
2 = ½ pupa — ½ adult
3 = sumpernumerary pupa
4 = ½ larva — pupa.

Percent control, defined as the percentage of treated insects which failed to perpetuate themselves, was also measured. In determining percent control, account was made of treated insects that failed to reach adulthood for one reason or another, plus those that failed to lay eggs, or that laid sterile eggs.

For the cabbage looper, an acetone solution containing 100 micrograms of the test compound in 5 microliters of solution was applied topically to the entire length of the body of a late-fifth-stage larva. Normally 10 larvae were treated per test. The treated larvae were then fed until they pupated. The pupae were examined under a microscope, checking for any larval characteristics in the pupae (juvenilization). Percent juvenilization as well as the mortality readings were made. The pupae were incubated until the adult (if any) emerged. These adults were then checked as to egg laying and percent laying fertile eggs. Mortality of the adults was determined. Juvenilization, degree of juvenilization and percent control were determined. The degree of juvenilization was measured based on the following:

0 = normal-apearing pupa
1 = ½ larva — ½ pupa; no prolegs; pupoid thorax
2 = ½ larva — ½ pupa; prolegs; pupoid thorax
3 = supernumerary larva For the yellow fever mosquito, late-fourth-stage larvae of the mosquitos were placed in a cup containing 30 ml of deionized water having 6 ppm of the test material dissolved therein. About 20 larvae were used per test. The larvae were fed and allowed to pupate. The pupae were examined under a microscope for retention of larvae characteristics (juvenilization). The live pupae were kept until the adult mosquitos emerged, mated and laid eggs. The percent fertile eggs was determined. A count was made at each stage for mortality, i.e., larval, pupal and adult.

The results of the tests are tabulated in Table II.

carbon atoms substituted with 0 to 4 halogen atoms of atomic number 9 to 35 or alkenyl of 2 to 6 carbon atoms substituted with 0 to 4 halogen atoms of atomic number 9 to 35, $R^3$ is haloalkyl or haloalkenyl of up to 10 to carbon atoms substituted with 1 to 5 halogen atoms of atomic number 9 to 35 or phenyl substituted with 0 to 2 halogen atoms of atomic number 9 to 35 or

TABLE I

| Compound | Elemental Analysis — % | | | | | | Melting Point, °C |
|---|---|---|---|---|---|---|---|
| | Calculated | | | Found | | | |
| | Cl | N | S | Cl | N | S | |
| 2-(4-chlorophenylsulfenylmercapto)-4-methyl pyrimidine | 13.2 | — | 23.8 | 14.4 | — | 23.1 | 80–82 |
| 2-(1,2,2,2-tetrachloroethylsulfenylmercapto) pyrimidine | 45.7 | — | 20.1 | 45.4 | — | 20.5 | 50–51 |
| 2-(1,1,2,2-tetrachloroethylsulfenylmercapto) pyrimidine | | | | | | | |
| 2-(1,1,2,2-tetrachloroethylsulfenylmercapto)-4,6-dimethyl pyrimidine | — | 8.3 | — | — | 7.6 | — | 53–54 |
| 2-(1,1-dimethyl-2,2-dichloroethylsulfenylmercapto)-6-hydroxy pyrimidine hydrochloride | 33.1 | — | 20.0 | 29.6 | — | 19.4 | 200 (dec) |
| 2-(1,1-dimethyl-2,2-dichloroethylsulfenylmercapto)-4,6-dimethyl pyrimidine | 23.9 | — | 21.6 | 24.4 | — | 21.6 | 82.5–83.5 |
| 2-(1,1-dimethyl-2,2-dichloroethylsulfenylmercapto)-4-propyl-6-hydroxy pyrimidine hydrochloride | 17.6 | — | 29.6 | 17.5 | — | 29.3 | 144–171 (dec) |
| 2-(1,1,2,2-tetrachloroethylsulfenylmercapto)-6-hydroxy pyrimidine hydrochloride | 48.9 | — | 17.7 | 47.1 | — | 17.0 | 116–126 |
| 2-(1,2,2,2-tetrachloroethylsulfenylmercapto)-4-metyl pyrimidine | 43.77 | — | 19.79 | 43.60 | — | 18.65 | Oil |
| 2-(1,1-dimethyl-2,2-dichlorosulfenylmercapto)-4-methyl pyrimidine | 25.04 | — | 22.64 | 26.75 | — | 21.48 | Oil |

TABLE II

| | Dock Beetle | | | Cabbage Looper | | | Yellow Fever Mosquito | | |
|---|---|---|---|---|---|---|---|---|---|
| | Conc. (μg/ insect) | Juvenili- zation % (Degree) | % Con- trol (A) | (μg/ insect) | Juvenili- zation % (Degree) | % Con- trol (A) | Conc. (ppm) | Juvenili- zation % (Degree) | % Con- trol (A) |
| 2-(1,1,2,2-tetrachloroethylsulfenylmercapto)-4-methyl pyrimidine | 50 | 80 (4) | 95 | 10 | 30 (1.6) | 100 | 6.6 | 0 (0) | 100 |
| 2-(1,1,2,2-tetrachloroethylsulfenylmercapto-)4-hydroxy-6-propyl pyrimidine hydrochloride | 100 | 0 (—) | 70 | — | — | — | — | — | — |
| 2-(1,2,2,2-tetrachloroethylsulfenylmercapto) pyrimidine | — | — | — | 100 | 20 (1) | 100 | — | — | — |
| 2-(1,1,2,2-tetrachloroethylsulfenylmercapto) pyrimidine | — | — | — | 100 | 80 (1) | 80 | — | — | — |
| 2-(1,1,2,2-tetrachloroethylsulfenylmercapto)-4,6-dimethyl pyrimidine | 20 | — | 60 | 30 | 100 (1.5) | 100 | 15 | 0 (—) | 90 |
| 2-(1,1-dimethyl-2,2-dichloroethylsulfenyl-mercapto)-4,6-dimethyl pyrimidine | 20 | — | 50 | 250 | — | 30 | — | — | — |
| 2-(1,1,2,2-tetrachloroethylsulfenyl-mercapto)-6-hydroxy pyrimidine hydrochloride | 20 | 10 (2) | 100 | — | — | — | — | — | — |
| 2-(1,2,2,2-tetrachloroethylsulfenyl-mercapto)-4-methyl pyrimidine | — | — | — | 100 | 20 (1) | 40 | — | — | — |
| N-methyl-N-(4,6-dimethylpyrimido-2-sulfenyl-mercapto) formamide | 20 | 0 (—) | 90 | 100 | 60 (1) | 100 | — | — | — |
| 2-(trichloromethylsulfenylmercapto)-4-methyl pyrimidine | — | — | — | 30 | 50 (1) | 50 | — | — | — |

(A) Percent control refers to the percentage of treated insects that failed to reach adulthood for any reason, plus those that failed to lay eggs, plus those that laid sterile eggs; in effect, the percent treated insects that failed to perpetuate themselves.

What is claimed is:

1. A method of killing insects which comprises contacting pre-adult insects with a metamorphosis-inhibiting amount of a compound of the formula

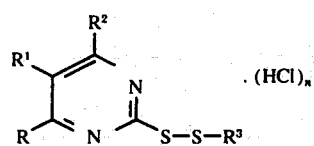

wherein R, $R^1$ and $R^2$ are individually hydrogen, halogen of atomic number 9 to 35, hydroxy, alkyl of 1 to 6 alkyl groups of 1 to 4 carbon atoms.

2. The method of claim 1 wherein $R^1$ is hydrogen, R and $R^2$ are individually hydrogen, hydroxy or alkyl of 1 to 4 carbon atoms, $R^3$ is haloalkyl of 1 to 4 carbon atoms substituted with 1 to 5 chlorine atoms, haloalkenyl of 2 to 4 carbon atoms substituted with 1 to 5 chlorine atoms or phenyl substituted with 0 to 2 chlorine atoms or alkyl groups of 1 to 4 carbon atoms.

3. The method of claim 1 wherein R is hydrogen or methyl, $R^1$ is hydrogen, $R^2$ is hydrogen, hydroxy or alkyl of 1 to 3 carbon atoms and $R^3$ is tetrachloroethyl or trichloromethyl.

4. The method of claim 3 wherein R is methyl, $R^2$ is hydrogen and $R^3$ is 1,1,2,2-tetrachloroethyl.

* * * * *